(12) United States Patent
Blackwell et al.

(10) Patent No.: US 8,409,291 B2
(45) Date of Patent: Apr. 2, 2013

(54) LATERALLY EXPANDABLE INTERBODY SPINAL FUSION IMPLANT

(75) Inventors: Jonathan Blackwell, Arlington, TN (US); Anthony Melkent, Memphis, TN (US); Kidong Yu, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 68 days.

(21) Appl. No.: 13/082,181

(22) Filed: Apr. 7, 2011

(65) Prior Publication Data

US 2012/0259416 A1  Oct. 11, 2012

(51) Int. Cl.
*A61F 2/44* (2006.01)

(52) U.S. Cl. .................................. 623/17.16; 623/17.15

(58) Field of Classification Search .... 623/17.11–17.16; 606/99, 102, 86 A, 90
See application file for complete search history.

(56) References Cited

U.S. PATENT DOCUMENTS

| | | | | |
|---|---|---|---|---|
| 6,039,761 | A * | 3/2000 | Li et al. | 623/17.16 |
| 6,258,125 | B1 * | 7/2001 | Paul et al. | 623/17.11 |
| 2006/0142858 | A1 * | 6/2006 | Colleran et al. | 623/17.11 |
| 2008/0243255 | A1 * | 10/2008 | Butler et al. | 623/17.16 |
| 2011/0029085 | A1 * | 2/2011 | Hynes et al. | 623/17.16 |
| 2011/0295372 | A1 * | 12/2011 | Peterman et al. | 623/17.16 |

* cited by examiner

*Primary Examiner* — Eduardo C Robert
*Assistant Examiner* — Lynnsy Schneider

(57) ABSTRACT

A spinal implant particularly adapted for lateral expansion while disposed in the disc space between adjacent vertebrae. The implant includes a first frame member pivotally linked to a second frame member via at least one, and preferably multiple, pivoting links. The implant may be inserted into the disc space in a collapsed configuration using a lateral approach, and then expanded in the anterior-posterior direction (lateral to insertion direction) to a deployed configuration where the first and second frame members are farther apart. The implant may be expanded by holding one frame member and pushing on the other frame member or one or more proximal links linking the two frame members.

20 Claims, 12 Drawing Sheets

LATERALLY EXPANDABLE INTERBODY SPINAL FUSION IMPLANT

BACKGROUND

The present invention relates generally to medical devices and procedures for orthopedic surgery, particularly to spinal implants associated with spinal interbody fusion.

A wide variety of spinal fusion devices are used following partial or total discectomies for stabilization of the spine at that site. Many such devices are secured in the disc space directly between the endplates of the adjacent vertebrae. Some of these devices are changed in height during installation. For example, some of the implants described in U.S. Patent Application Publication No. 2009/0198337 are adapted for implantation in the intervertebral disc space, and are changed in height during implantation. The ability to change height is advantageous in many situations, but such implants typically have a fixed lateral width. Accordingly, such implants may not be ideal for use where it is desired to laterally expand the implant, such as to better distribute the loads on the implant and spine, when using a lateral approach to implantation. Thus, while such implants are suitable for many situations, there remains a need for alternative designs.

SUMMARY

In one embodiment, the present invention is directed to a spinal implant particularly adapted for lateral expansion while disposed in the disc space between adjacent vertebrae. The implant includes a first frame member pivotally linked to a second frame member via at least one, and preferably multiple, pivoting links. The implant may be inserted into the disc space in a collapsed configuration using a lateral approach, and then expanded in the anterior-posterior direction (lateral to insertion direction) to a deployed configuration where the first and second frame members are farther apart.

In one embodiment, the present invention is directed to a spinal implant for insertion in a disc space between adjacent vertebrae. The implant includes a first frame member movably coupled to a second frame member. The first frame member comprises a first longitudinal axis, an outboard face, and inferior and superior faces. The first longitudinal axis extends from a first proximal end section to a first distal end section, with a first intermediate section disposed therebetween. The first outboard face faces generally opposite the second frame member. The inferior and superior faces are disposed on opposing sides of the first outboard face and face in generally opposite directions. The superior face has a first array of anti-backout protrusions extending upward away from the implant. The inferior face has a second array of anti-backout protrusions extending downward away from the implant. The second frame member comprises a second longitudinal axis, a second outboard face, and superior and inferior faces. The second longitudinal axis extends from a second proximal end section to a second distal end section, with a second intermediate section disposed therebetween. The second outboard face faces generally opposite the first frame member. The inferior and superior faces are disposed on opposing sides of the second outboard face and face in generally opposite directions. The superior face of the second frame member has a third array of anti-backout protrusions extending upward away from the implant. A first rigid link pivotally interconnects the first and second frame members. The first link is mounted to the first frame member for rotation relative thereto about a first vertical pivot axis. A second link movably interconnects the first and second frame members and is longitudinally spaced from the first link. The implant is laterally expandable in an expansion direction normal to the first pivot axis from a collapsed configuration to a deployed configuration. The expansion direction is advantageously normal to the first longitudinal axis. In the collapsed configuration 1) the first and second longitudinal axes are disposed relatively closer together; and 2) the first and second arrays of anti-backout protrusions of the first frame member are a first distance apart. In the deployed configuration 1) the first and second longitudinal axes are disposed relatively farther apart; and 2) the first and second arrays of anti-backout protrusions of the first frame member are the first distance apart.

In some embodiments, the first and second frame members have respective inboard faces that are in contact in the collapsed configuration. The first link may be mounted to the second frame member for rotation relative thereto about a second pivot axis. A third link may pivotally mounted to first and second proximal flanges of the first and second frame members, respectively, for rotation relative to the first frame member about the first pivot axis and for rotation relative to the second frame member about the second pivot axis; the third link vertically spaced from the first link with a gap formed therebetween. The first frame member may be taller in a direction parallel to the first pivot axis than the second frame member when viewed along their respective longitudinal axes. The first array of anti-backout protrusions may be configured to resist, when engaged with the corresponding vertebra, proximal displacement of the first frame member more than distal displacement of the first frame member.

In some embodiments, the present invention provides an expandable spinal implant for insertion in a disc space between adjacent vertebrae. The implant includes a first frame member, a second frame member, and two rigid links. The first frame member is moveably coupled to the second frame member and comprises a first longitudinal axis, an outboard face, and inferior and superior faces. The first longitudinal axis extends from a first proximal end section to a first distal end section, with a first intermediate section disposed therebetween. The first outboard face faces generally opposite the second frame member. The inferior and superior faces are disposed on opposing sides of the first outboard face and face in generally opposite directions. The superior face has a first array of upwardly extending anti backout protrusions thereon in the first intermediate section. The inferior face having a second array of downwardly extending anti backout protrusions thereon in the first intermediate section. The first proximal section includes a first proximal flange. The second longitudinally extending frame member includes a second longitudinal axis, a second outboard face, inferior and superior faces. The second longitudinal axis extends from a second proximal end section to a second distal end section, with a second intermediate section disposed therebetween. The second outboard face faces generally opposite the first frame member. The inferior and superior faces are disposed on opposing sides of the second outboard face and facing in generally opposite directions. The superior face has a third array of upwardly extending anti backout protrusions thereon in the second intermediate section. The inferior face has a fourth array of downwardly extending anti backout protrusions thereon in the second intermediate section. The second proximal section includes a second proximal flange. The first rigid link is pivotally mounted to the first proximal flange for rotation about a first pivot axis relative to the first frame member. The first link is also pivotally mounted to the second proximal flange for rotation about a second pivot axis relative to the second frame member. The second rigid link is pivotally mounted to the first distal end section for rotation about a third pivot axis relative to the first frame member. The second link is also pivotally mounted to the second distal end section for rotation about a fourth pivot axis relative to the second frame member. The first longitudinal axis extends through the first and third pivot axes. The second longitudinal axis extends through the second and fourth pivot axes. The implant is expandable from a collapsed configuration to a deployed configuration. In the collapsed configuration 1) the first and second frame members are disposed relatively closer together; 2) the outboard faces of the first and second frame members are a first distance apart; and 3) a first theoretical line from the first pivot axis to the second pivot axis forms an included obtuse first angle relative to a first longitudinal axis. In the deployed configuration 1) the first and second frame members are disposed relatively farther apart; 2) the outboard faces of the first and second frame members are a second distance apart; the second distance larger than the first distance; 3) the first theoretical line forms an included second angle relative to the first longitudinal axis; the second angle smaller than the first angle. The first theoretical line may be perpendicular to the first longitudinal axis in the deployed configuration.

The implant may be configured such that the intermediate section of the first frame member further includes comprises one or more vertical notches extending a majority of the distance between the inferior and superior faces. With the implant in the deployed configuration, a central opening may have a perimeter defined by the first frame member, the first link, the second frame member, and the second link. The distal end sections of the first and second frame members narrow in the distal direction.

In various embodiments, the present invention has one or more of the above attributes, alone or in any combination.

DETAILED DESCRIPTION

In one embodiment, the present invention is directed to a spinal implant particularly adapted for lateral expansion while disposed in the disc space between adjacent vertebrae. The implant includes a first frame member pivotally linked to a second frame member via at least one, and preferably multiple, pivoting links. The implant may be inserted into the disc space in a collapsed configuration using a lateral approach, and then laterally expanded to a deployed configuration where the first and second frame members are farther apart.

Figure 1:
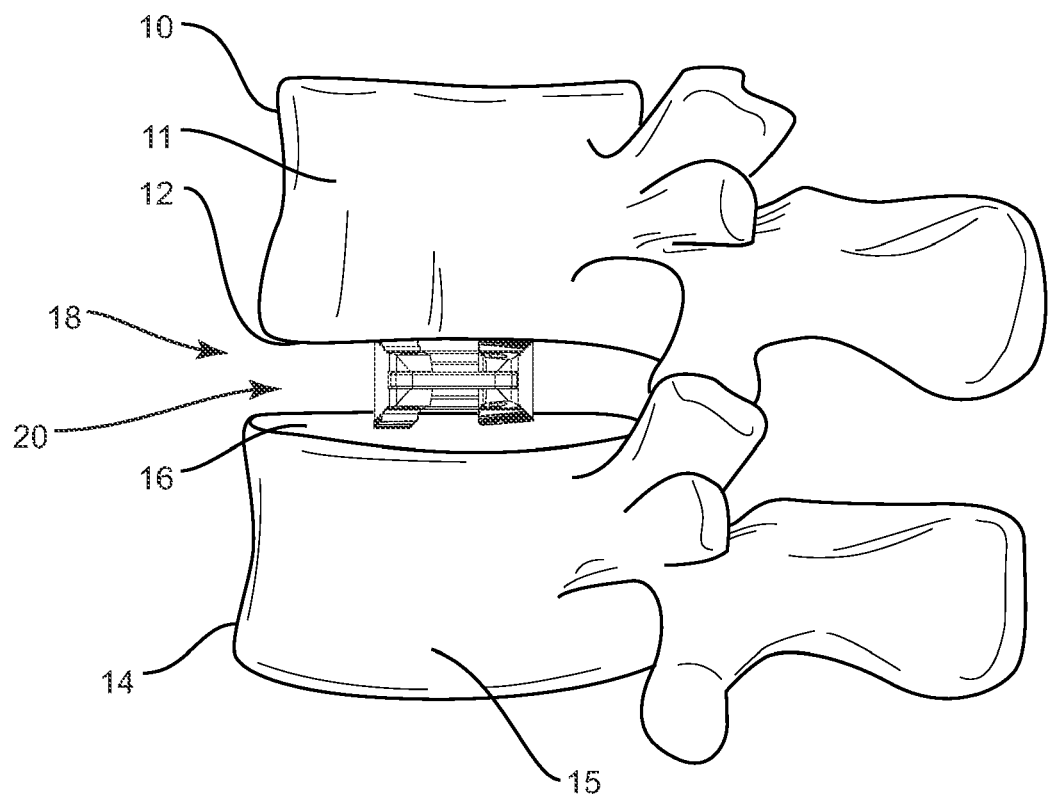
FIG. 1 shows an expanded implant in a disc space.
Figure 2:
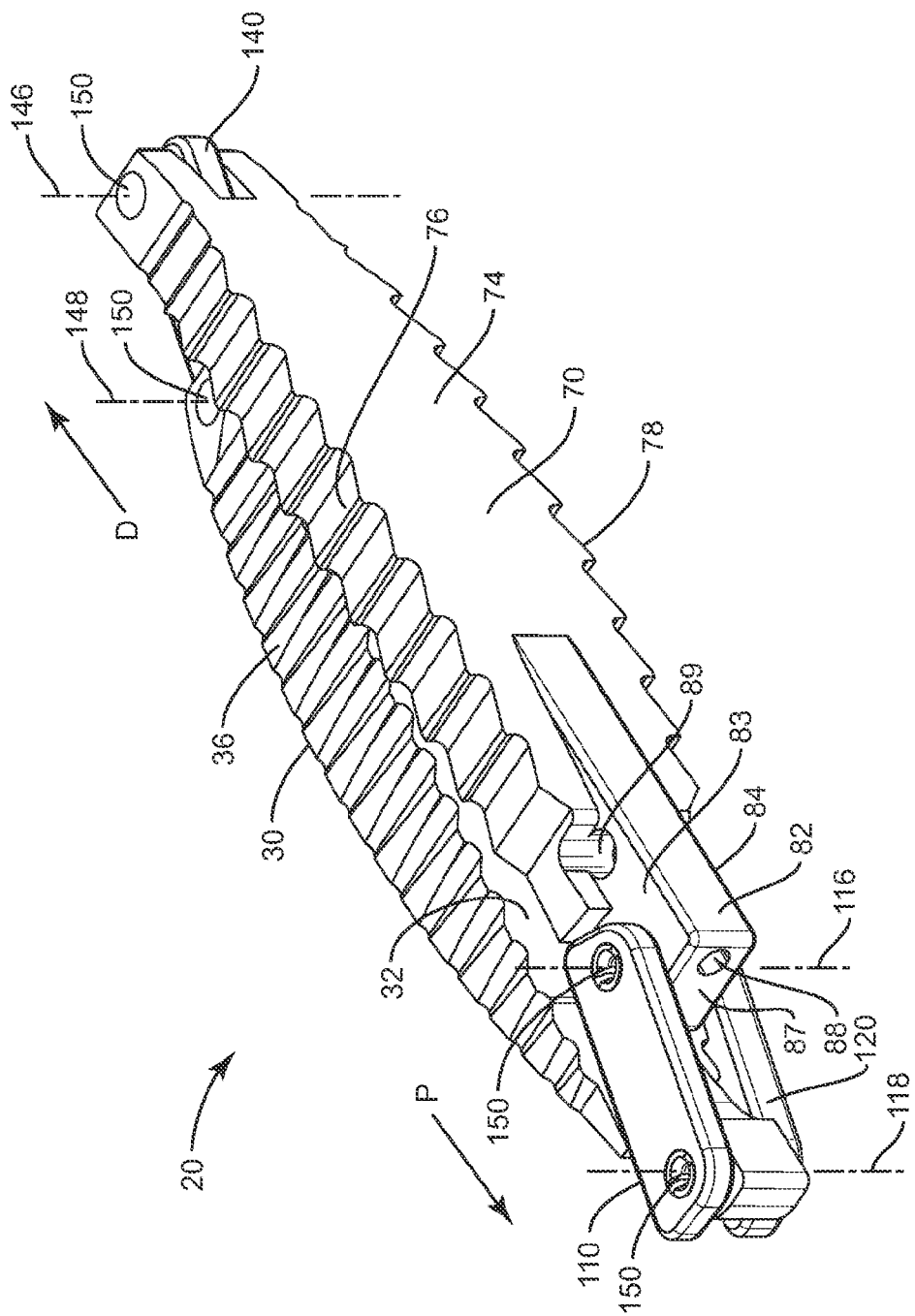
FIG. 2 shows a perspective view of an exemplary implant in a collapsed configuration.
Figure 3:
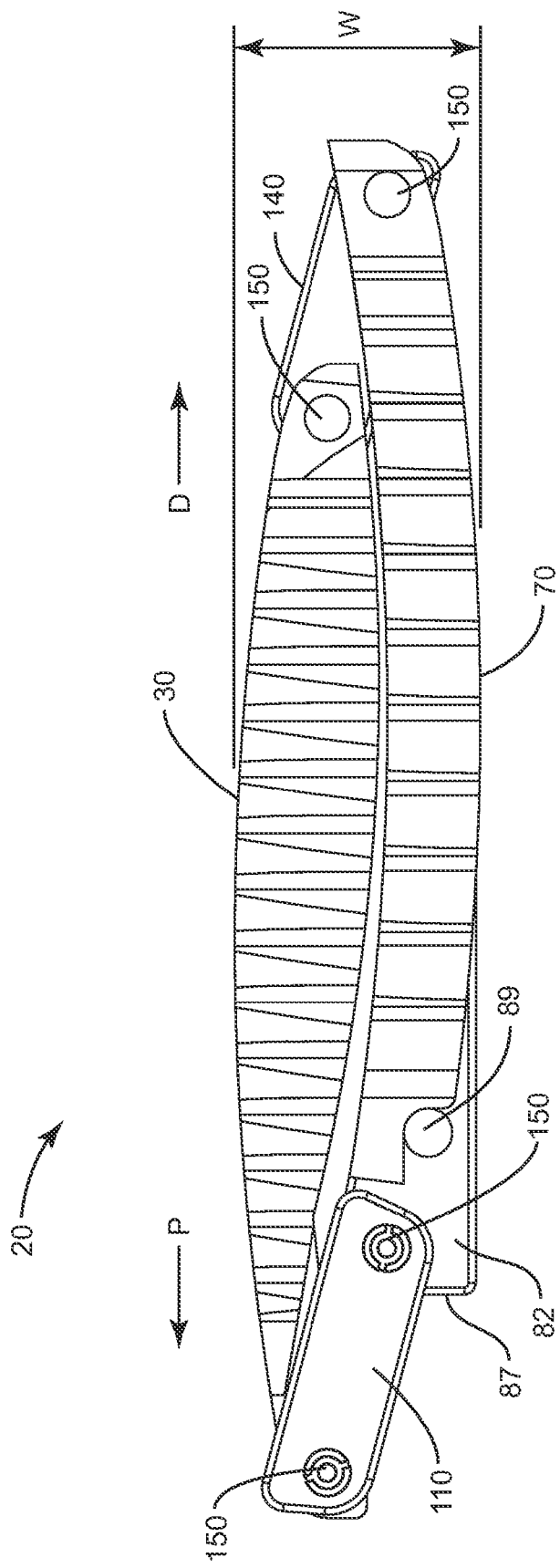
FIG. 3 shows a top view of the implant of FIG. 2 in the collapsed configuration.

In order to provide illustrative context, the following discussion will focus primarily on use of the invention for spinal surgery in the lumbar region of the spine, but it should be understood that the invention may alternatively or additionally be used in other regions of the spine. FIG. 1 depicts adjacent vertebrae 10,14 of the lumbar region of a human spinal column. Each vertebrae 10,14 comprises a corresponding vertebral body 11,15, a superior articular process, a transverse process, an inferior articular process, and a spinous process. In addition, between vertebral bodies 11,15 is a space 18 normally occupied by an intervertebral disc and bounded by the endplates 12,16 of the vertebral bodies. Due to various conditions, such as a collapsed disc, it may be desired to place an implant in the disc space 18 in order to provide proper structural continuity between the vertebral bodies 11,15, such as to promote fusion of the spinal segment. The spinal implant 20 of the present invention may be placed in the disc space 18 and then expanded laterally (i.e., expanded in a direction generally parallel to the endplates 12,16).

The implant 20 may take a variety of forms, with one example being shown in FIGS. 2-6. For ease of reference during the following discussion, the direction indicated by arrow P in FIG. 2 will be referred to as the proximal direction as it is closest to the surgeon, while the direction indicated by arrow D will be referred to as the distal direction as it is farthest from the surgeon. The implant 20 of FIGS. 2-6 includes a posterior frame member 30, an anterior frame member 70, two proximal links 110,120, a distal link 140, and interconnecting pins 150, as shown in the exploded view of FIG. 6.

Figure 7:
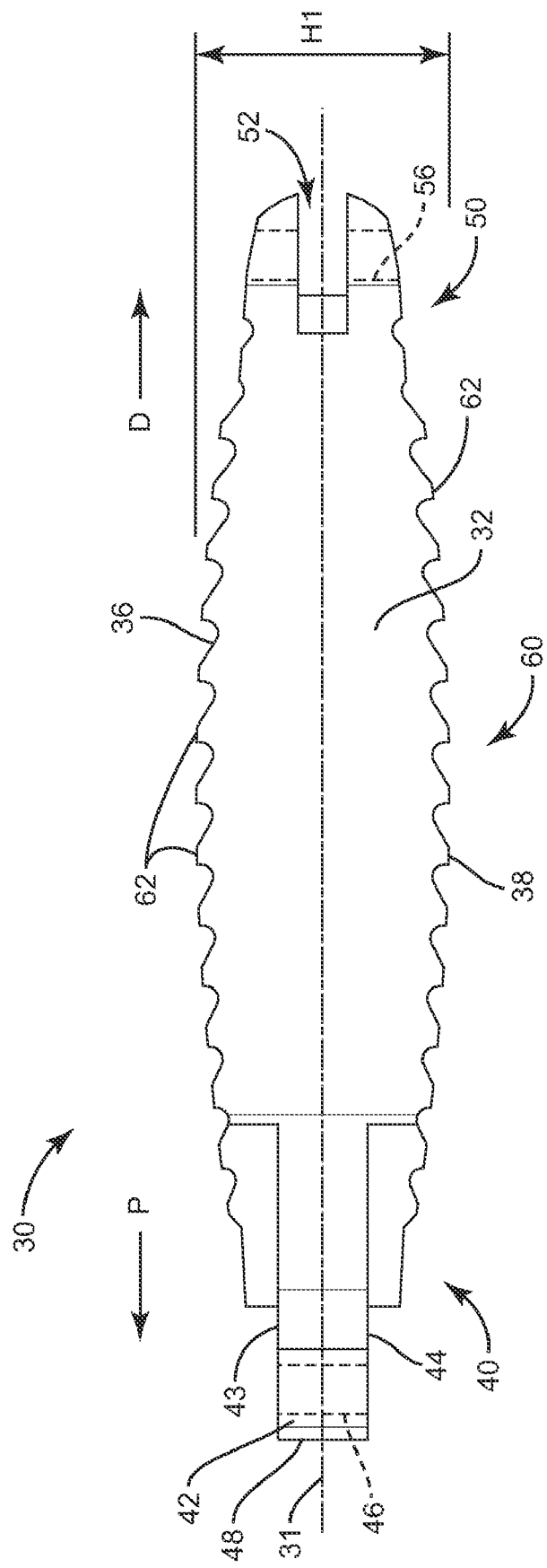
FIG. 7 shows a side view of the posterior frame member of FIG. 2, looking at the inboard face.
Figure 8:
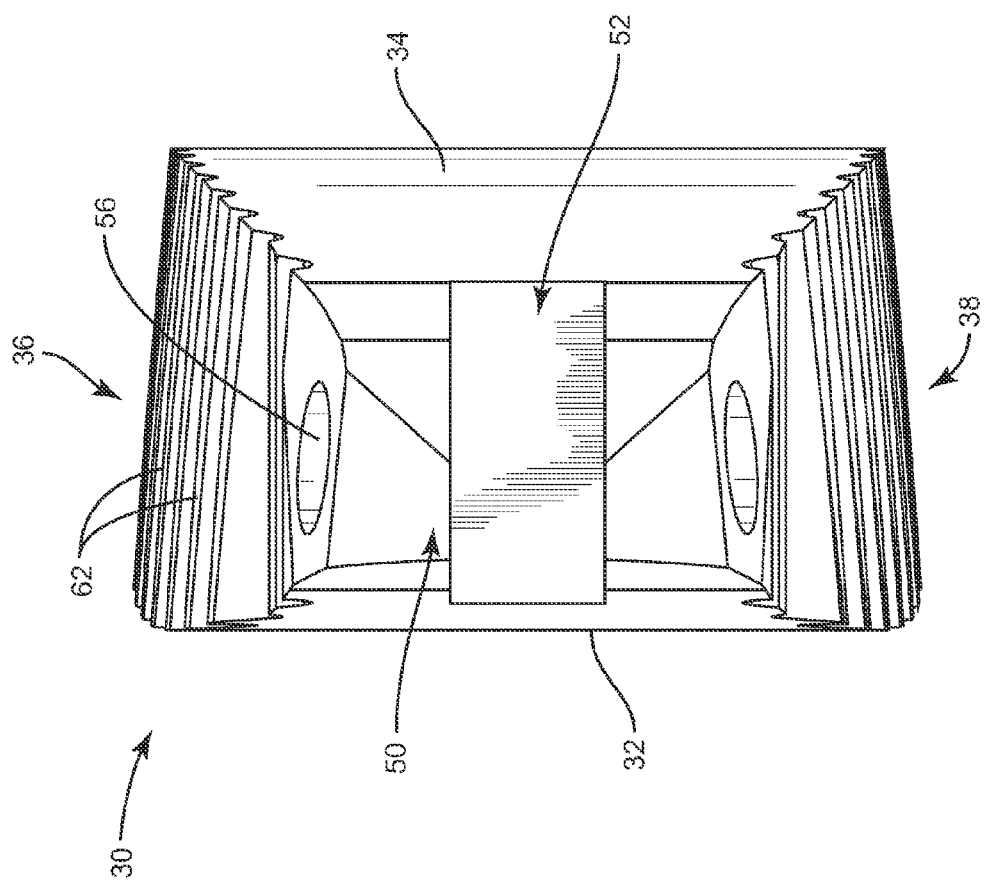
FIG. 8 shows a front view of the posterior frame member of FIG. 7.
Figure 9:
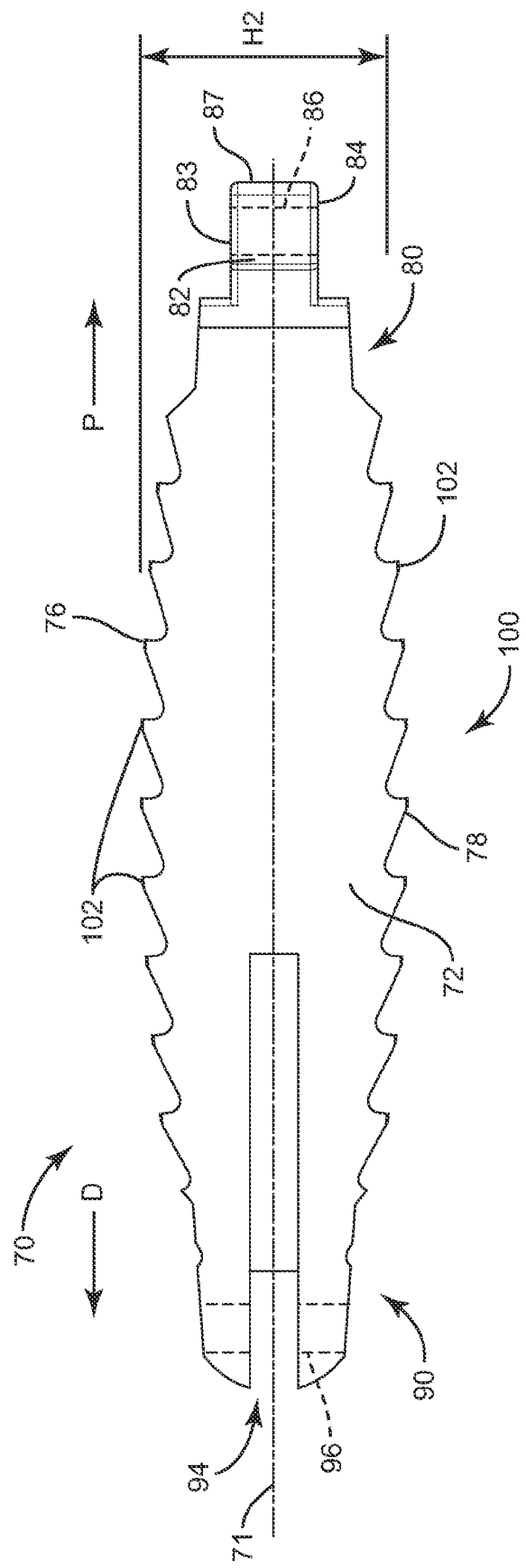
FIG. 9 shows a side view of the anterior frame member of FIG. 2 looking at the inboard face.
Figure 10:
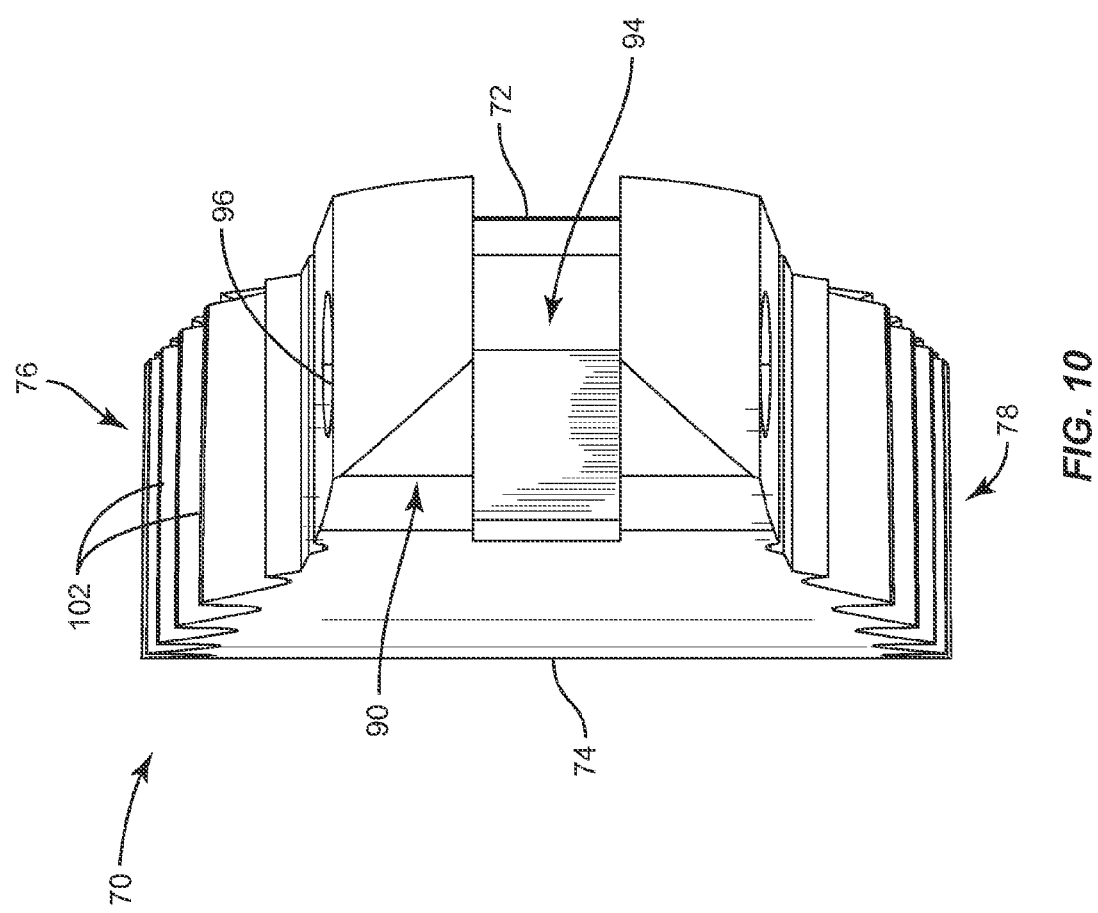
FIG. 10 shows a front view of the anterior frame member of FIG. 9.

The posterior frame member 30 is elongate generally along its longitudinal axis 31 from a proximal end section 40, through an intermediate section 60, to a distal end section 50. The posterior frame member 30 has an inboard face 32, an outboard face 34, an upper or superior face 36, and a lower or inferior face 38. The inboard face 32 faces the anterior frame member 70 and is advantageously convexly curvate. The outboard face 34 faces generally opposite the inboard face 32 (i.e., away from the anterior frame member 70) and is also advantageously convexly curvate. See FIG. 3 and FIG. 5. The inboard face 32 and outboard face 34 may be smooth if desired. The superior face 36 may advantageously be convexly curvate, at a relatively shallow curvature relative to the curvature of the inboard and outboard faces 32, 34. The superior face 36, at least in the intermediate section 60, advantageously includes an array of upwardly extending anti-back-out protrusions 62 that are designed to engage endplate 12 of superior vertebra 10. These protrusions 62 may take a variety of forms, such as the array of ridges as shown in FIGS. 2-6, or an array of teeth or barbs, etc. The protrusions 62 are advantageously configured so that they provide greater resistance to proximal movement than distal movement of the posterior frame member 30 when engaged with endplate 12. To this end, the protrusions 62 may taper vertically, such as with a triangular or pyramid shape in side view, with a backward orientation slanting in the proximal direction P. See FIG. 7. In addition, if the protrusions 62 are ridges as illustrated, the ridges may have their peaks slope down in height in the direction of the outboard face 34, if desired. See FIG. 8. Similar reductions in height may apply to other forms of protrusions 62 as well. Likewise, the inferior face 38 may advantageously be convexly curvate, again at a relatively shallow curvature relative to the curvature of the inboard and outboard faces 32, 34. The inferior face 38 advantageously includes, at least in the intermediate section, an array of downwardly extending anti-backout protrusions 62 similar to the protrusions 62 of superior face 36, which are designed to engage the endplate 16 of the inferior vertebra 14. The proximal end section 40 advantageously includes a proximally extending flange 42 that terminates in a proximal endface 48. The proximal flange 42 includes a through hole 46 for receiving a pivot pin 150 that may extend from the upper surface 43 to the lower surface 44 of the proximal flange 42. The distal end section 50 is advantageously tapered on its distal end, and includes a slot 52 formed between two spaced apart flanges for receiving link 140, as discussed further below. This slot 52 advantageously extends into the intermediate section 60, and tapers toward the inboard face 32. See FIG. 6. The distal end section 50 also includes hole 56 for receiving pivot pin 150, as discussed further below. Longitudinal axis 31 extends through the center of holes 46,56.

The anterior frame member 70 is elongate generally along its longitudinal axis 71 from a proximal end section 80, through an intermediate section 100, to a distal end section 90. The anterior frame member 70 has an inboard face 72, an outboard face 74, an upper or superior face 76, and a lower or inferior face 78. The inboard face 72 faces the posterior frame member 30 and is advantageously concavely curvate. The outboard face 74 faces generally opposite the inboard face 72 (i.e., away from the posterior frame member 30) and is also advantageously convexly curvate. The inboard face 72 and outboard face 74 may be smooth if desired. The superior face 76 may advantageously be convexly curvate, at a relatively shallow curvature relative to the curvature of the inboard and outboard faces 72,74. The superior face 76, at least in the intermediate section 100, advantageously includes an array of upwardly extending anti-backout protrusions 102 that are similar to the protrusions 62 of posterior frame member 30, but which advantageously do not slope downward in height toward the outboard face 74 (e.g., are horizontal). Similar to protrusions 62, protrusions 102 are designed to engage the endplate 12 of the superior vertebra 10 and are advantageously configured provide greater resistance to proximal movement than to distal movement of the anterior frame member 70. Likewise, the inferior face 78 may advantageously be convexly curvate, again at a relatively shallow curvature relative to the curvature of the inboard and outboard faces 72,74. The inferior face 78 likewise advantageously includes, at least in the intermediate section 100, an array of downwardly extending anti-backout protrusions 102 that are similar to protrusions 102 associated with the superior face 76 and which are designed to engage the endplate 16 of the inferior vertebra 14. The proximal end section 80 advantageously includes a proximally extending flange 82 that terminates in a proximal endface 87. The proximal flange 82 includes a through hole 86 for receiving a pivot pin 150 that may extend from the upper surface 83 to the lower surface 84 of the proximal flange 82. In addition, the proximal flange 82 may include additional holes to aid in releasably mating with a surgical instrument, such as blind holes 89 in upper surface 83 and lower surface 84, and a bore hole 88 in endface 87 that extends parallel to longitudinal axis 71. Bore hole 88 may be threaded if desired. The distal end section 90 is advantageously similarly configured with distal end section 50 of posterior frame member 30, with hole 96 for pivot pin 150 and slot 94, but slot 94 may be relatively straighter and shorter than slot 52 so as to not extend into intermediate section 100. Longitudinal axis 71 extends through the center of holes 86,96.

Figure 4:
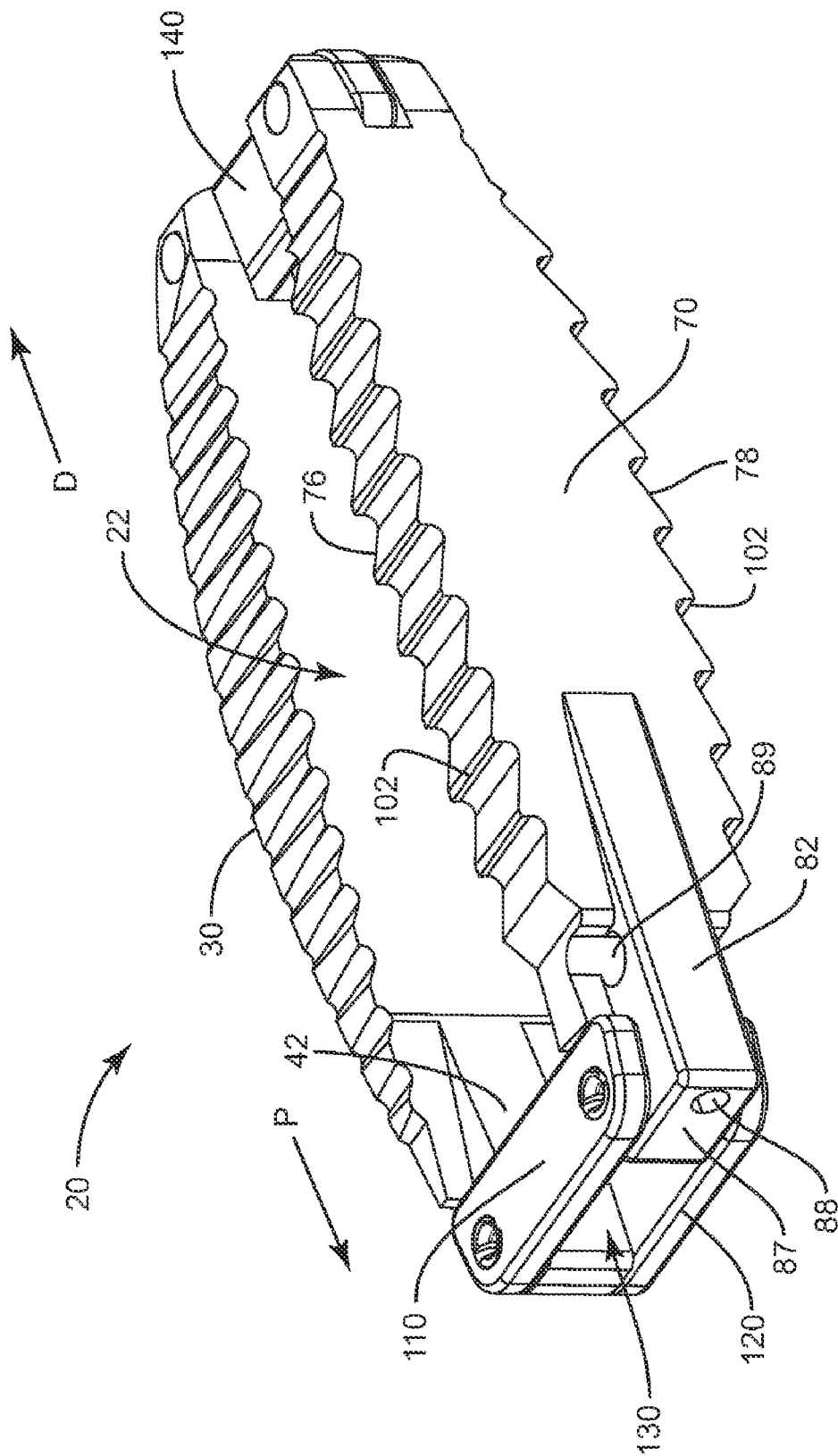
FIG. 4 shows a perspective view of the implant of FIG. 2 in a deployed configuration.
Figure 5:
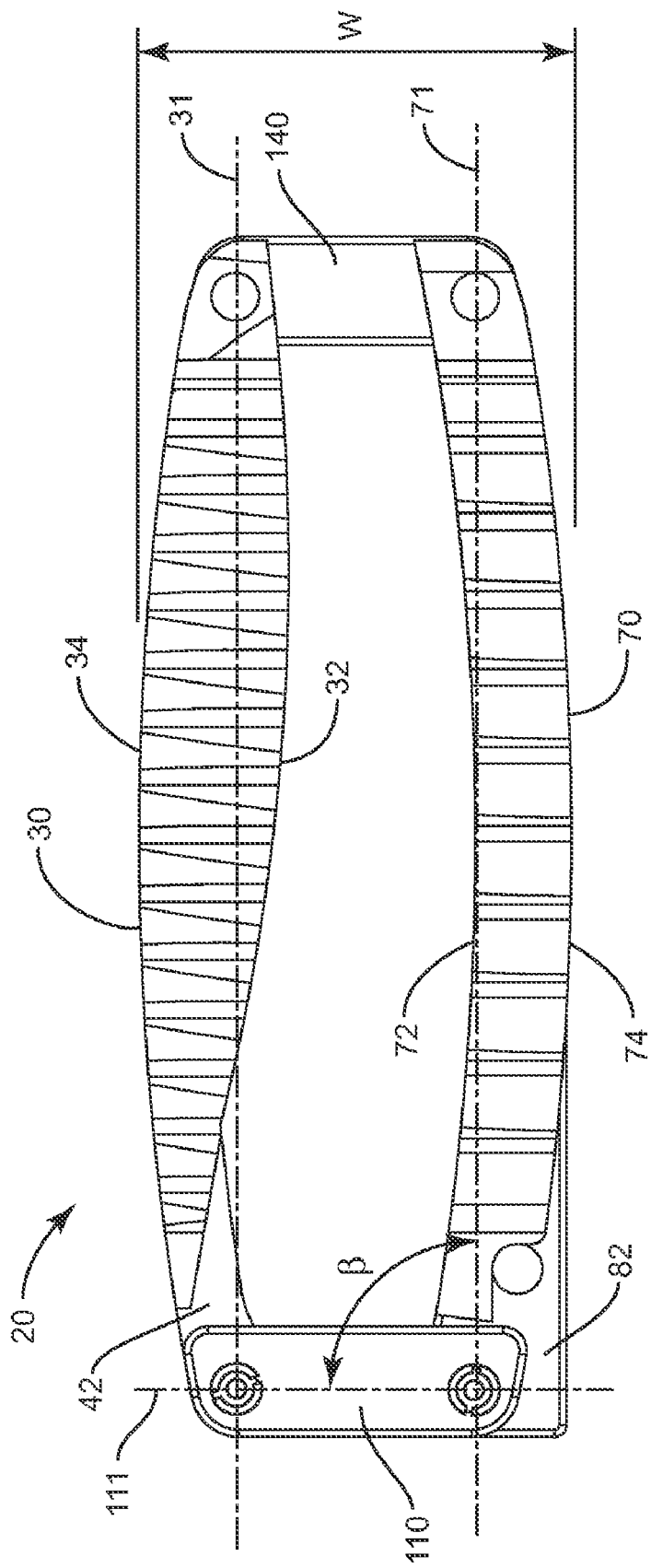
FIG. 5 shows a top view of the implant of FIG. 2 in the deployed configuration.
Figure 6:
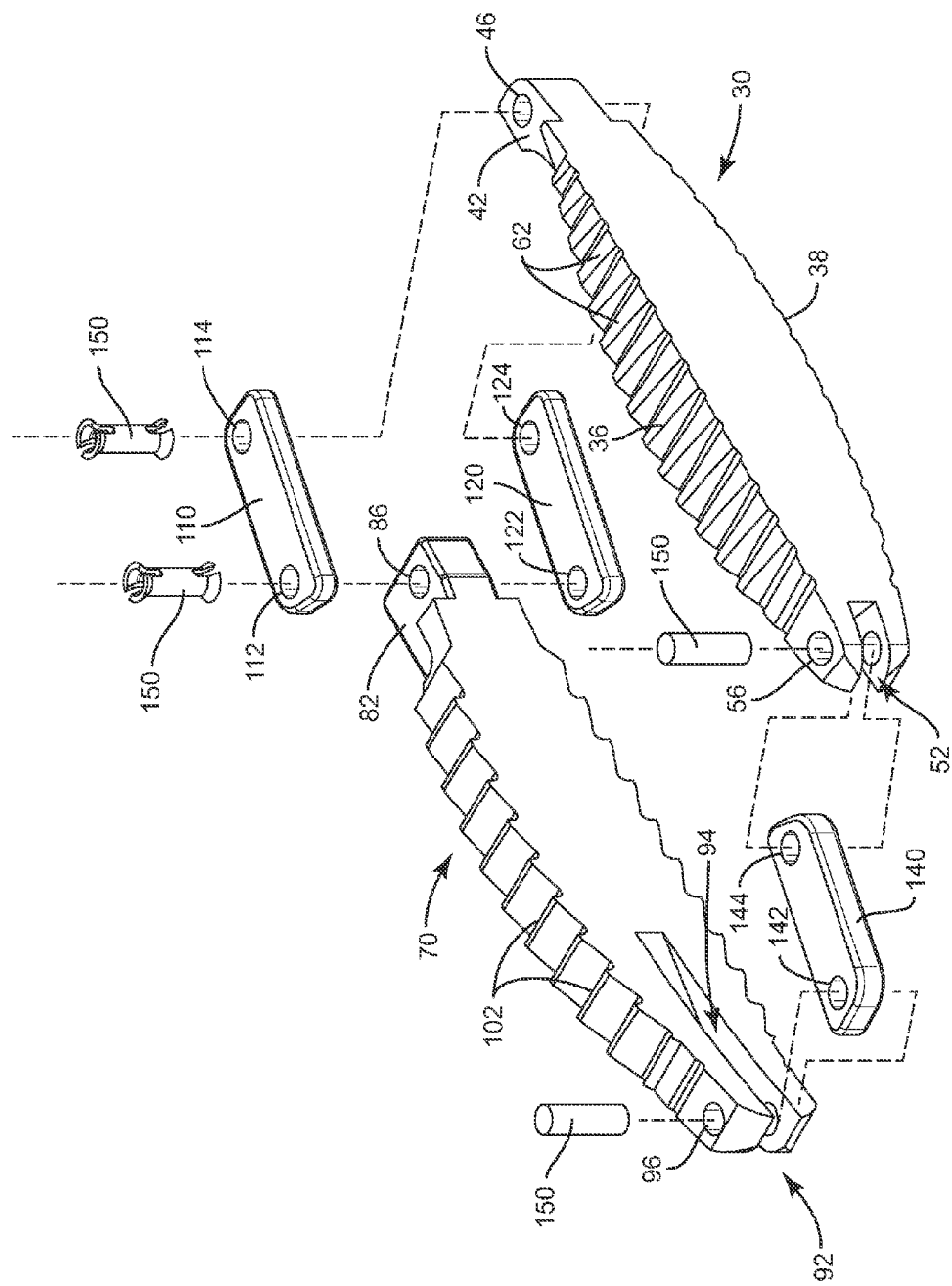
FIG. 6 shows a exploded view of the implant of FIG. 2 rotated about a vertical axis to better show some features.

Proximal links 110,120 pivotally interconnect the proximal end sections 40,80 of the frame members 30,70. The upper link 110 rests partially against the superior surface 43 of proximal flange 42 and partially on superior surface 83 of proximal flange 82. The upper link 110 includes an anterior hole 112 and a posterior hole 114, with an axis 111 extending through the centers thereof. The anterior hole 112 is aligned with hole 86 in proximal flange 82 of anterior frame member 70, while posterior hole 114 is aligned with hole 46 in proximal flange 42 of posterior frame member 30. Hole 112 is designed to receive pin 150 to mount link 110 to anterior frame member 70 such that link 110 may pivot relative to anterior frame member 70 about pivot axis 116. Hole 114 is designed to receive pin 150 to mount link 110 to posterior frame member 30 such that link 110 may pivot relative to posterior frame member 30 about pivot axis 118. As can be appreciated, this pivoting action results in angle $\beta$ between axis 71 of anterior frame member 70 and axis 111 of link 110 changing from a relatively larger obtuse angle in the collapsed configuration (FIGS. 2-3) (to allow for a minimum overall width W of the implant 20 when collapsed) to a smaller angle, such as 90°±30° (advantageously approximately 90°) in the deployed configuration (FIGS. 4-5). The lower link 120 also includes holes 122,124 for receiving pins 150, and may advantageously be identical to upper link 110. A vertical gap 130 is defined between the upper link 110 and lower link 120, which may be used to access the space or central opening 22 between the inboard faces 32,72 when the implant 20 is deployed, as discussed further below.

The distal link 140 pivotally interconnects the distal end sections 50,90 of the frame members 30,70. The distal link 140 extends into slot 94 in anterior frame member 70 and slot 52 of posterior frame member 30. The distal link 140 may be similar to links 110,120, and includes holes 142,144 for receiving pivot pins 150 for pivoting link 140 about axes 146,148 respectively, similar to that discussed above.

Pins 150 are used to pivotally mount links 110,120,140 to frame members 30,70. These pins may take any suitable form known in the art, such as straight pins, rivets, expandable head pins, and the like. The pins may be press-fit into the frame members 30,70 and have a sliding fit with the links 110,120, 140, or vice-versa, or a combination thereof. For links that are mounted to exterior surfaces of the frame members 30,70, such as links 110,120 in the illustrated embodiment, the pins 150 are advantageously upset, staked, or otherwise configured to prevent migration of the links along the corresponding pivot axes.

The implant 20 is laterally expandable from a collapsed configuration (FIGS. 2-3) where the posterior frame member 30 is disposed relatively closer to the anterior frame member 70 to an expanded configuration (FIGS. 4-5) where the posterior frame member 30 is disposed relatively farther from the anterior frame member 70. Comparing FIG. 2 and FIG. 4, it can be seen that the width W of the implant 20 is relatively smaller in the collapsed configuration than in the deployed configuration. For example, the width W of the implant 20 in the collapsed configuration may be approximately eight to fifteen millimeters, and the width W in the deployed configuration may be approximately eighteen to thirty millimeters. For example, in one embodiment, the width W may change from approximately eleven millimeters in the collapsed configuration to approximately eighteen millimeters in the deployed configuration. In the collapsed configuration, the convex inboard face 32 of the posterior frame member 30 advantageously rests in the shallow recess formed by the concave inboard face 72 of the anterior frame member 70. Indeed, in some embodiments, the inboard faces 32,72 abut one another in the collapsed configuration. Also, the links 110,120,140 are angled proximally relative to the anterior frame member 70, so that posterior frame member 30 is disposed slightly proximally relative to the anterior frame member 70. The extended and angled nature of slot 52 allows link 140 to be disposed in such a manner while allowing the implant 20 to have a minimal width. Similarly, the boundary between the proximal flange 42 and the proximal portion of the intermediate section 60 of the posterior frame member 30 should be configured to allow the links 110,120 to be angled appropriately.

To deploy the implant 20, the posterior frame member 30 is move distally and laterally. For example, a surgical instrument (not shown) is used to apply a force to link 110 and/or link 120 to cause the links 110,120 to rotate distally (clockwise in FIGS. 2-3) relative to anterior frame member 70 about corresponding axis 116. This rotation about pivot axis 116, and the corresponding rotation of link 140 about pivot axis 146, causes posterior frame member 30 to move distally and laterally relative to anterior frame member 70. As a result, the inboard faces 32,72, and the longitudinal axes 31,71, are spread apart. In the fully deployed configuration, the links 110,120,140 are advantageously disposed generally perpendicular to longitudinal axes 31,71. Further, if the links 110, 120,140 are identical, or at least the spacing between axes 116,118 compared to the distance between axes 146,148 are the same, then axes 31, 71 advantageously remain parallel to each other in the both the deployed and collapsed configurations. The links 110,120,140 and the inboard faces 32,72 of frame members 30,70 cooperate to form the perimeter of a central opening 22 (when viewed from above) that is open upwardly and downwardly. The central opening 22 may be accessed from the proximal direction via gap 130 between links 110,120.

The implant 20 may be inserted into the disc space 18 in the collapsed configuration and then laterally expanded to the deployed configuration. Prior to insertion, the implant 20 may be attached to a surgical instrument (not shown). A portion of the surgical instrument may extend into hole 88 to aid in maintaining longitudinal alignment of the surgical instrument and the anterior frame member 70. The hole 88 and the corresponding portion of the instrument may be threaded, or a different releasable connection interface, including a smooth interface, may be used. In addition, the surgical instrument may engage blind holes 89 or otherwise releasably grip anterior flange 82 to prevent relative rotation of the anterior frame member 70 and the instrument. The implant 20 is then inserted into the disc space 18, typically from a lateral approach, such as during a direct lateral lumbar interbody fusion (DLIF) procedure. As can be appreciated, other procedures, such as anterior lumbar inner body fusion (ALIF) and transforaminal lumbar interbody fusion (TLIF) may also employ the implant 20. In order to facilitate this, the distal end sections 50,90 of the frame members 30,70 may be tapered, either individually or collectively, to form a self-dilating shape such as a bullet-type shape. During insertion, the instrument may be pushing distally directly on the anterior frame member 70, with the posterior frame member 30 being moved distally via the mechanical linkage of links 110,120,140. Due to their configuration, the protrusions 62,102 on the frame members 30,70 may engage the endplates 12,16 to allow the distal movement of the implant 20, but inhibit proximal movement of the implant 20. Once the anterior frame member 70 is positioned as desired, one or more surgical instruments are used to push the posterior frame member 30 distally, while maintaining the position of the anterior frame member 70, so as to laterally expand the implant 20. For example, the insertion instrument may continue to grip the anterior frame member 70, while another surgical instrument is urged distally against link 110 and/or link 120. This distal pushing causes the links 110,120 to rotate. This rotation results in link 110 rotating about pivot axis 116 (clockwise in FIGS. 2-3 relative to anterior frame member 70) and about pivot axis 118 (counter-clockwise in FIGS. 2-3 relative to posterior frame member 30). Similarly, link 120 rotates about pivot axes 116,118. Due to the force transmission through the frame members 30,70, link 140 is also rotated about pivot axes 146,148. This rotation of the links 110,120,140 causes the posterior frame member 30 to move distally and laterally relative to the anterior frame member 70 to the deployed position. Once the implant 20 is deployed, bone growth material may be inserted into the central opening 22 via gap 130. The surgical instrument(s) are then removed from the implant 20. If desired, another implant 20 may then be inserted into the disc space 18, such as from the contra-lateral side.

It should be noted that the superior faces 36,76 and the inferior faces 38,78 of the frame members 30,70 may be flat, but are advantageously convexly curved as discussed above. In addition, the smaller overall height H1 of the posterior frame member 30, compared to the overall height H2 of anterior frame member 70, allows the implant 20 to better accommodate the lordodic curve of the spine.

The frame members 30,70, links 110,120,140, and pins 150 may be formed of suitable biologically compatible material(s), such as titanium and its alloys, stainless steel, polymers such as PEEK, and other materials known in the art. The various components may be made from the same or different materials, as desired. The links 110,120,140 are advantageously rigid.

Figure 11:
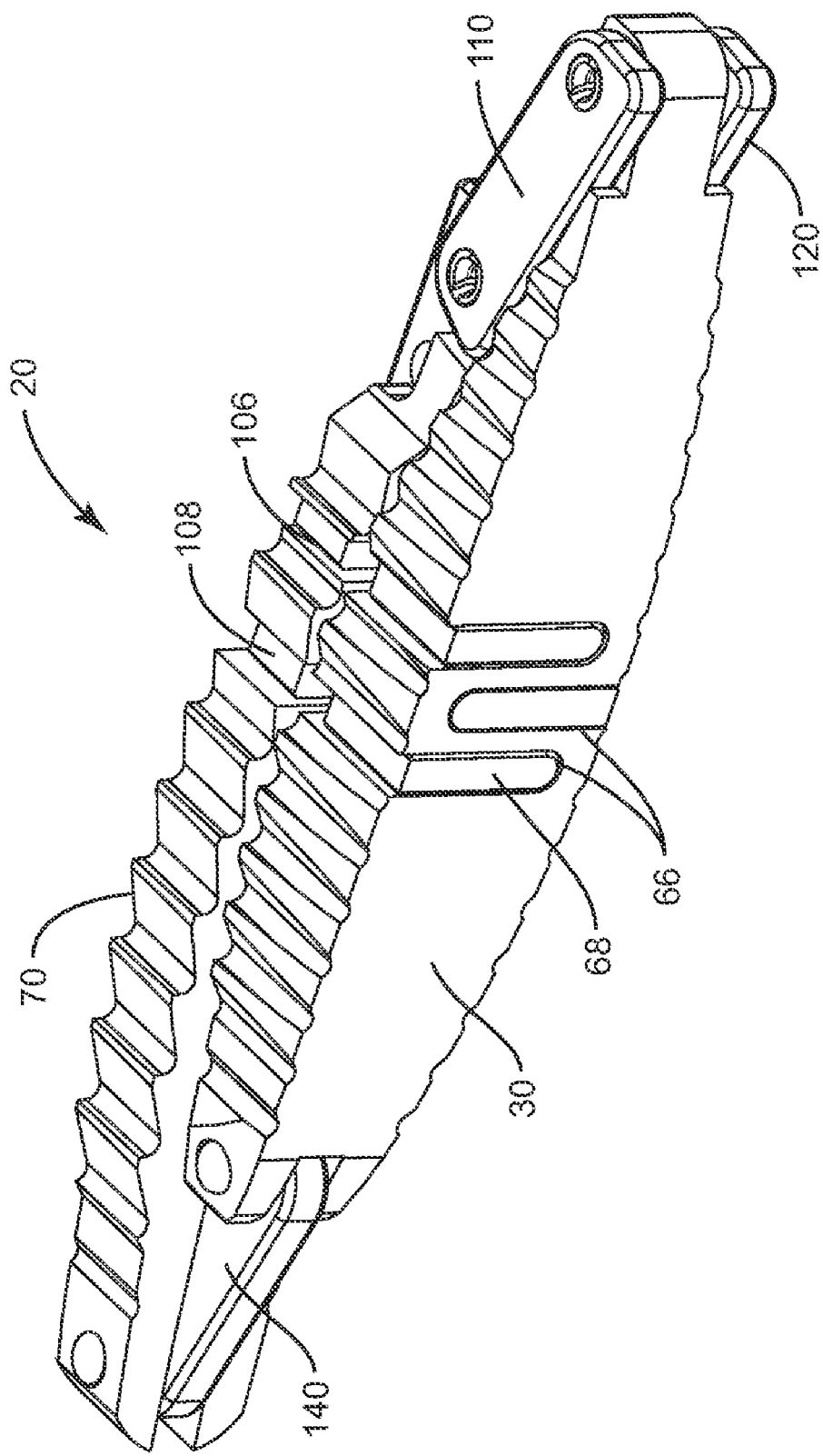
FIG. 11 shows an alternative embodiment of the implant.
Figure 12:
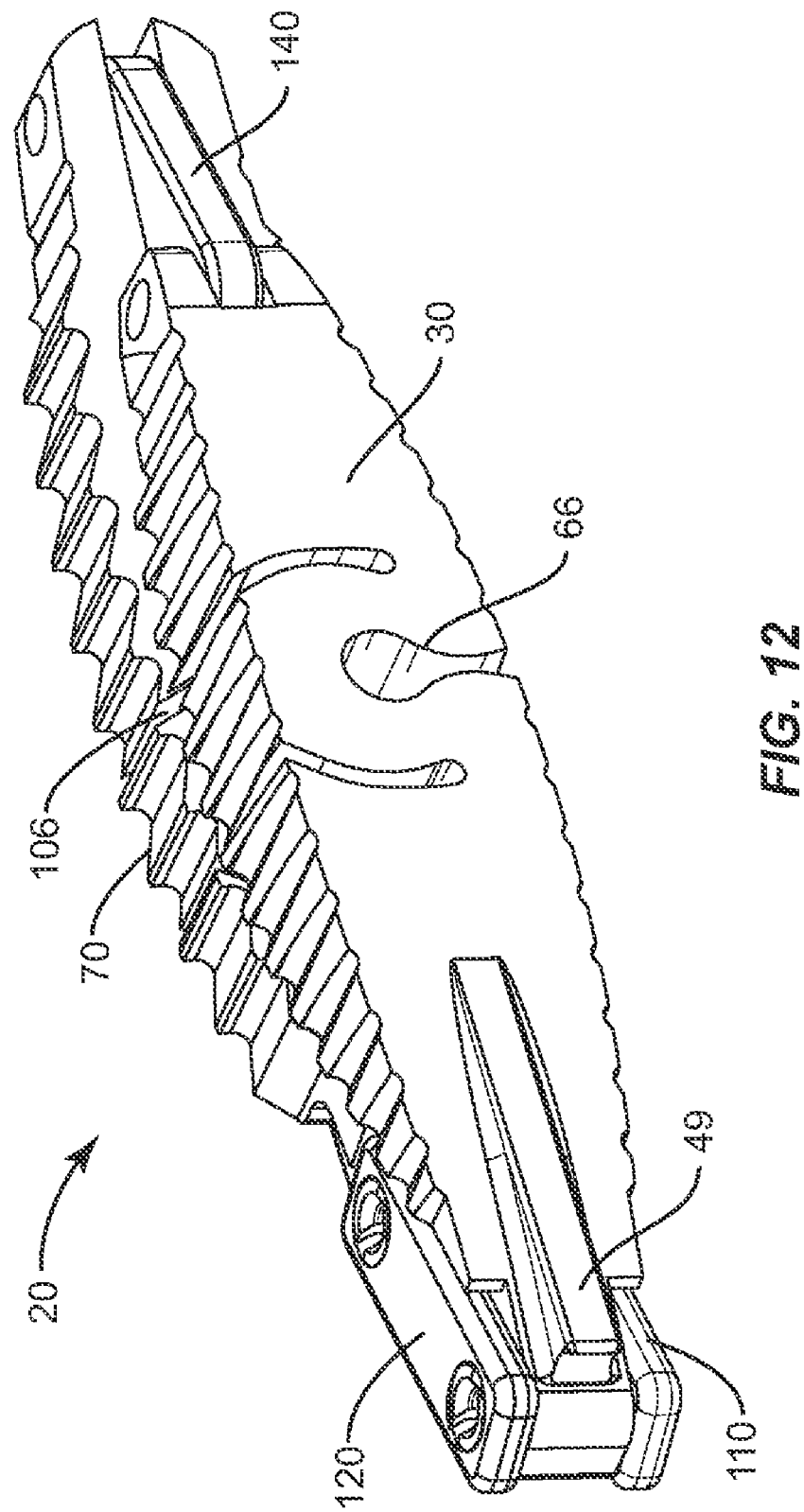
FIG. 12 shows an alternative embodiment of the implant.

In some embodiments, the frame members 30,70 may include notches 66 in order to provide some flexibility in longitudinal bending. For example, the frame members 30,70 shown in FIG. 11 include vertical U-shaped notches 66, advantageously from both the superior faces 36,76 and the inferior faces 38,78, that extend most of the height of the corresponding frame members 30,70, leaving only a narrow connecting sections which are relatively more flexible than the adjacent thick portions of the frame members 30,70. The notches 66, if present, are advantageously present on both frame members 30,70, to allow bending along a bending axis in the collapsed configuration. If desired, the notches 66 may have inserts 68 therein, with the inserts 68 being a relatively flexible material with a lower modulus of elasticity than the material of the frame members 30,70 to adjust the flexibility to the desired level. Suitable pliant materials for the inserts 68 include polyurethane, silicone, and the like. See U.S. Patent Application Publication No. 2011/0029083 for further details of notches 66 and suitable materials. The notches 66 need not be U-shaped or linearly vertical, as shown by the embodiment of FIG. 12.

In some embodiments, the implant 20 may be expanded by pushing against links 110,120. However, such is not required. In some embodiments, the surgeon may alternatively or additionally use an instrument to push against the endface 48 of the posterior frame member 30 to expand implant 20. In other embodiments, such as the embodiment of FIG. 12, the proximal section 40 of the posterior frame member 30 may further include a second flange 49 that may be alternatively or additionally pressed against to expand the implant 20.

The discussion above has been in the context of the implant 20 having two proximal links 110,120 and a single distal link 140. While such an arrangement is believed to be advantageous, such is not required in all embodiments. Any number of distal and proximal links may be used, provided there is at least one rigid proximal link and at least one rigid distal link. For example, the distal end of the implant 20 may have multiple links, making the implant 20 somewhat symmetrical, or there may be only one proximal link and multiple distal links.

The discussion above has generally been in the context of deploying the implant 20 by holding the anterior frame member 70 in position and pushing against links 110,120 to move the posterior frame member 30. While such an approach is believed advantageous, the posterior frame member 30 may alternatively be moved by pushing distally directly against the posterior frame member 30 (e.g., at endface 48), rather than (or in addition to) against links 110,120. Likewise, the discussion has been in terms of positioning the anterior frame member 70 and then laterally expanding the implant 20 by moving the posterior frame member 30 posteriorly. However, the implant 20 could alternatively be deployed by reversing this such that the posterior frame member 30 is positioned and the anterior frame member 70 is then moved anteriorly. In some embodiments, either frame member 30,70 may be proximal relative to the other at insertion, and the other frame member 70,30 may be directly or indirectly pushed or pulled into the deployed configuration.

The discussion above has been in the context of the teeth 62 on the posterior frame member 30 being potentially truncated as compared with the teeth 102 on the anterior frame member 70. This arrangement is believed advantageous when positioning the anterior frame member 30 and effectively moving the posterior frame member 30 relative to the anterior frame member 30 and the endplates 12,16 during expansion. However, the relative aggressiveness of the teeth 62,102 could be reversed if the process is changed to positioning the posterior frame member 70 and moving the anterior frame member 70 relative to the posterior frame member 30 and the endplates 12,16 during expansion. Alternatively, the teeth 62,102 may be substantially similar in aggressiveness.

The discussion above has illustratively described the insertion process as inserting the implant 20 into the disc space 18 with the superior faces 36,76 and inferior faces 38,78 facing relatively directly at endplates 12,16 of the adjacent vertebrae 10,14. Thus, the axes 31,71 lie in a theoretical plane generally parallel to the endplates 12,16 when first inserted into the disc space 18. This orientation may be thought of as the horizontal orientation because the frame members 30,70 are side-by-side horizontally relative to the disc space 18. However, in some embodiments, the implant 20 may oriented differently during its initial insertion into the disc space 18. For example, the implant 20 may be inserted into the disc space 18 in a vertical orientation, with one of the frame members 30,70 disposed directly above the other frame member 70,30. The implant 20 is then rotated to the horizontal orientation while in the disc space 18, and then laterally expanded as described above.

All U.S. patents and patent application publications mentioned above are hereby incorporated herein by reference in their entirety.

The present invention may, of course, be carried out in other specific ways than those herein set forth without departing from the scope of the invention. The present embodiments are, therefore, to be considered in all respects as illustrative and not restrictive, and all changes coming within the meaning and equivalency range of the appended claims are intended to be embraced therein.

What is claimed is:

1. A spinal implant for insertion in a disc space between adjacent vertebrae, comprising: a first frame member moveably coupled to a second frame member; the first frame member comprising: a first longitudinal axis extending from a first proximal end section to a first distal end section, with a first intermediate section disposed therebetween; a first outboard face facing generally opposite the second frame member; inferior and superior faces disposed on opposing sides of the first outboard face and facing in generally opposite directions; the superior face having a first array of anti-backout protrusions extending upward away from the implant; the inferior face having a second array of anti-backout protrusions extending downward away from the implant; the second frame member comprising: a second longitudinal axis extending from a second proximal end section to a second distal end section, with a second intermediate section disposed therebetween; a second outboard face facing generally opposite the first frame member; inferior and superior faces disposed on opposing sides of the second outboard face and facing in generally opposite directions; the superior face of the second frame member having a third array of anti-backout protrusions extending upward away from the implant; a first rigid link pivotally interconnecting the first and second frame members; the first link mounted to the first frame member for rotation relative thereto about a first vertical pivot axis; a second link movably interconnecting the first and second frame members and longitudinally spaced from the first link; wherein the implant is laterally expandable in an expansion direction normal to the first pivot axis from a collapsed configuration to a deployed configuration; wherein, in the collapsed configuration: the first and second longitudinal axes are disposed relatively closer together; the first and second arrays of anti-backout protrusions of the first frame member are a first distance apart; wherein, in the deployed configuration: the first and second longitudinal axes are disposed relatively farther apart; the first and second arrays of anti-backout protrusions of the first frame member are the first distance apart, wherein the first link is mounted to the second frame member for rotation relative thereto about a second pivot axis;

a third link pivotally mounted to first and second proximal flanges of the first and second frame members, respectively, for rotation relative to the first frame member about the first pivot axis and for rotation relative to the second frame member about the second pivot axis; the third link vertically spaced from the first link with a gap formed therebetween.

2. The spinal implant of claim 1 wherein the first and second frame members have respective inboard faces that are in contact in the collapsed configuration.

3. The spinal implant of claim 1 wherein the first frame member further comprises an inboard face that faces the second frame member; wherein the inboard and outboard faces of the first frame member are longitudinally curved.

4. The spinal tool of claim 3 wherein the inboard and outboard faces of the first frame member curve generally parallel to one another.

5. The spinal tool of claim 1 wherein the first frame member is taller in a direction parallel to the first pivot axis than the second frame member when viewed along their respective longitudinal axes.

6. The spinal implant of claim 1 wherein the first array of anti-backout protrusions includes a plurality of ridges.

7. The spinal implant of claim 1 wherein the intermediate section of the first frame member further comprises one or more vertical notches extending a majority of the distance between the inferior and superior faces.

8. The spinal implant of claim 7 further comprising inserts disposed in the notches; the inserts having a lower modulus of elasticity than the first and second frame members.

9. The spinal implant of claim 1 wherein the protrusions forming the third array taper to lessen in height toward the outboard face of the second frame member.

10. The spinal implant of claim 1 wherein, with the implant in the deployed configuration, a central opening has a perimeter defined by the first frame member, the first link, the second frame member, and the second link.

11. The spinal implant of claim 1 wherein the first frame member has an inboard face facing the second frame member; wherein the second frame member has an inboard face facing the first frame member; wherein the inboard face of the first frame member is longitudinally concavely curved; wherein the outboard face of the first frame member is longitudinally convexly curved.

12. The spinal implant of claim 11 wherein the inboard and outboard faces of the second frame member are longitudinally convexly curved.

13. The spinal implant of claim 12 wherein a curvature of the inboard face of the second frame member approximately matches a curvature of the inboard face of the first frame member.

14. The spinal implant of claim 1 wherein the first array of anti-backout protrusions are configured to resist, when engaged with the corresponding vertebra, proximal displacement of the first frame member more than distal displacement of the first frame member.

15. An expandable spinal implant for insertion in a disc space between adjacent vertebrae, comprising: a first frame member moveably coupled to a second frame member; the first frame member comprising: a first longitudinal axis extending from a first proximal end section to a first distal end section, with a first intermediate section disposed therebetween; a first outboard face facing generally opposite the second frame member; inferior and superior faces disposed on opposing sides of the first outboard face and facing in generally opposite directions; the superior face having a first array of upwardly extending anti-backout protrusions thereon in the first intermediate section; the inferior face having a second array of downwardly extending anti-backout protrusions thereon in the first intermediate section; the first proximal end section including a first proximal flange; the second frame member comprising: a second longitudinal axis extending from a second proximal end section to a second distal end section, with a second intermediate section disposed therebetween; a second outboard face facing generally opposite the first frame member; inferior and superior faces disposed on opposing sides of the second outboard face and facing in generally opposite directions;
the superior face having a third array of upwardly extending anti-backout protrusions thereon in the second intermediate section; the inferior face having a fourth array of downwardly extending anti-backout protrusions thereon in the second intermediate section; the second proximal section including a second proximal flange; a first rigid link pivotally mounted to a to surface of the first proximal flange for rotation about a first pivot axis relative to the first frame member; the first link also pivotally mounted to a top surface of the second proximal flange for rotation about a second pivot axis relative to the second frame member; a second rigid link pivotally mounted within a slot of to the first distal end section for rotation about a third pivot axis relative to the first frame member; the second link also pivotally mounted within a slot of the second distal end section for rotation about a fourth pivot axis relative to the second frame member; a third rigid link pivotally mounted to a bottom surface of the first proximal flange for rotation about the first pivot axis relative to the first frame member; the third link also pivotally mounted to a bottom surface of the second proximal flange for rotation about the second pivot axis relative to the second frame member; the first longitudinal axis extending through the first and third pivot axes; the second longitudinal axis extending through the second and fourth pivot axes; wherein the implant is expandable from a collapsed configuration to a deployed configuration; wherein, in the collapsed configuration: the first and second frame members are disposed relatively closer together; the outboard faces of the first and second frame members are a first distance apart; a first theoretical line from the first pivot axis to the second pivot axis forms an included obtuse first angle relative to a first longitudinal axis; wherein, in the deployed configuration: the first and second frame members are disposed relatively farther apart; the outboard faces of the first and second frame members are a second distance apart; the second distance larger than the first distance; the first theoretical line forms an included second angle relative to the first longitudinal axis; the second angle smaller than the first angle.

16. The spinal implant of claim 15 wherein the intermediate section of the first frame member further comprises one or more vertical notches extending a majority of the distance between the inferior and superior faces.

17. The spinal implant of claim 15 wherein the first theoretical line is perpendicular to the first longitudinal axis in the deployed configuration.

18. The spinal implant of claim 15 wherein, with the implant in the deployed configuration, a central opening has a perimeter defined by the first frame member, the first link, the second frame member, and the second link.

19. The spinal implant of claim 15 wherein the distal end sections of the first and second frame members narrow in the distal direction.

20. A spinal implant for insertion in a disc space between adjacent vertebrae, comprising: a first frame member moveably coupled to a second frame member; the first frame member comprising: a first longitudinal axis extending from a first proximal end section to a first distal end section, with a first intermediate section disposed therebetween; a first outboard face facing generally opposite the second frame member; inferior and superior faces disposed on opposing sides of the first outboard face and facing in generally opposite directions; the superior face having a first array of anti-backout protrusions extending upward away from the implant; the inferior face having a second array of anti-backout protrusions extending downward away from the implant; the second frame member comprising: a second longitudinal axis extending from a second proximal end section to a second distal end section, with a second intermediate section disposed therebetween; a second outboard face facing generally opposite the first frame member; inferior and superior faces disposed on opposing sides of the second outboard face and facing in generally opposite directions; the superior face of the second frame member having a third array of anti-backout protrusions extending upward away from the implant; a first rigid link pivotally interconnecting the first and second frame members; the first link mounted to the first frame member for rotation relative thereto about a first vertical pivot axis; a second link movably interconnecting the first and second frame members and longitudinally spaced from the first link, a first end of the second link being disposed within a first slot in the first distal end section and a second end of the second link being disposed within a second slot in the second distal end section, said first slot of the first frame member extending a greater distance into the first intermediate section than the second slot of the second frame member extends into the second intermediate section; wherein the implant is laterally expandable in an expansion direction normal to the first pivot axis from a collapsed configuration to a deployed configuration; wherein, in the collapsed configuration: the first and second longitudinal axes are disposed relatively closer together; the first and second arrays of anti-backout protrusions of the first frame member are a first distance apart; wherein, in the deployed configuration: the first and second longitudinal axes are disposed relatively farther apart; the first and second arrays of anti-backout protrusions of the first frame member are the first distance apart.

* * * * *